United States Patent
Fukushima

(10) Patent No.: US 8,052,900 B2
(45) Date of Patent: Nov. 8, 2011

(54) REACTIVE UV ABSORBER, UV-SCREEN FILM-FORMING CURABLE COATING SOLUTION, UV-SCREEN FILM, AND SUBSTRATE HAVING UV-SCREENING FUNCTION

(75) Inventor: Motoo Fukushima, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 70 days.

(21) Appl. No.: 12/611,423

(22) Filed: Nov. 3, 2009

(65) Prior Publication Data

US 2010/0108960 A1 May 6, 2010

(30) Foreign Application Priority Data

Nov. 4, 2008 (JP) ................. 2008-283039

(51) Int. Cl.
*F21V 9/04* (2006.01)
*F21V 9/06* (2006.01)
*G02B 5/22* (2006.01)
*G02B 5/26* (2006.01)

(52) U.S. Cl. ............. 252/589; 252/400.31; 106/287.1; 106/287.14; 427/164; 427/204; 427/387; 428/412; 428/429; 428/447; 524/588; 524/858; 524/859; 525/266; 528/12; 528/21; 528/29; 556/436

(58) Field of Classification Search .......... 252/589, 252/400.31; 428/447, 412, 429; 106/287.1, 106/287.14; 427/164, 204, 387; 524/588, 524/858, 859; 528/12, 21, 29; 525/266; 556/436

See application file for complete search history.

(56) References Cited

U.S. PATENT DOCUMENTS

| | | |
|---|---|---|
| 4,373,061 A | 2/1983 | Ching |
| 4,390,660 A | 6/1983 | Ashby |
| 4,436,924 A | 3/1984 | Ashby et al. |
| 4,525,426 A | 6/1985 | Anthony |
| 5,391,795 A | 2/1995 | Pickett |
| 6,497,964 B1 | 12/2002 | Matsumura et al. |
| 2003/0020049 A1 | 1/2003 | Payne et al. |
| 2008/0260664 A1 | 10/2008 | Walenzyk et al. |

FOREIGN PATENT DOCUMENTS

| | | |
|---|---|---|
| JP | 57-21390 A | 2/1982 |
| JP | 57-21476 A | 2/1982 |
| JP | 58-213075 A | 12/1983 |
| JP | 5-70397 A | 3/1993 |
| JP | 7-278525 A | 10/1995 |
| JP | 2000-160130 A | 6/2000 |
| JP | 3648280 B2 | 5/2005 |
| JP | 4092522 B2 | 5/2008 |

OTHER PUBLICATIONS

European Search Report issued in European Application No. 09174278.3 on Jan. 19, 2010.
Friedrich et al., "Synthesis and Test of Styrene-Cyclosiloxane and Butadiene-Cyclosiloxane Block Copolymers Containing Ultraviolet (UV) Absorber and Antioxidant Groups", Journal of Inorganic and Organometallic Polymers, 1991, vol. 1, No. 3, pp. 397-415.
Japanese Office Action dated Feb. 9, 2011 for Japanese Application No. 2008-283039.

*Primary Examiner* — Ling Choi
*Assistant Examiner* — Bijan Ahvazi
(74) *Attorney, Agent, or Firm* — Birch, Stewart, Kolasch & Birch, LLP

(57) ABSTRACT

A mixture of a benzophenone derivative having hydroxyl and alkoxysilyl groups and a benzophenone derivative having silyloxy and alkoxysilyl groups provides a reactive UV absorber which is unlikely to gel, stable during shelf storage, and curable. A coating solution comprising the UV absorber cures at room temperature to form a UV-screening film which has adhesion to glass and plastic substrates, scratch resistance, and bleed resistance, and maintains a UV-screening function over time.

7 Claims, No Drawings

REACTIVE UV ABSORBER, UV-SCREEN FILM-FORMING CURABLE COATING SOLUTION, UV-SCREEN FILM, AND SUBSTRATE HAVING UV-SCREENING FUNCTION

CROSS-REFERENCE TO RELATED APPLICATION

This non-provisional application claims priority under 35 U.S.C. §119(a) on Patent Application No. 2008-283039 filed in Japan on Nov. 4, 2008, the entire contents of which are hereby incorporated by reference.

TECHNICAL FIELD

This invention relates to novel ultraviolet (UV) absorbers, UV-screening film-forming coating solutions comprising the same, UV-screening films, and substrates having UV-screening function.

BACKGROUND ART

Among light emissions from sun, fluorescent lamps, Braun tubes and the like, UV rays in the short wavelength region of up to 400 nm have many detrimental effects, not only to the human body including sunburn, speckles, carcinogenesis and eyesight failure, but also to articles, including mechanical strength degradation, outer appearance degradation (e.g., fading), and discoloration of printed matter.

To address such problems, especially the problem that the UV transmitted by windows into buildings or automobiles causes degradation of interiors, fading of fabrics, and sunburn of the human body, it is required to control transmission of UV by windows. In such UV screening applications, there are used film, glass, and plastic articles which are provided with a UV-screening function by incorporating UV absorbers therein or by applying a coating solution containing a UV absorber onto a substrate to form a UV-screening film thereon. For the existing windows and substrates, it is a common practice to provide them with a UV-screening function by applying a coating solution containing a UV absorber thereto to form a UV-screening film.

UV absorbers used in the prior art include salicylic acid, benzophenone, benzotriazole and cyanoacrylate compounds. Since these conventional UV absorbers cannot form a coating by themselves, they are typically used as additives to binder components. Also, these UV absorbers will evaporate or volatilize off over a long period of service, resulting in substrates having a degraded UV-screening function. In order that coated substrates retain a UV-screening function for a long time, the UV absorbers must be used in larger amounts, which give rise to problems such as bleed-out of UV absorber onto the surface and clouding of the substrate.

It was thus proposed to incorporate silicon into UV absorbers for anchoring. Such approaches are successful to some extent. In order to incorporate UV absorbers into silicone resins with good heat resistance and light resistance, many attempts were made to react benzophenone UV absorbers with alkoxysilanes.

For instance, JP 4092522 discloses a curable UV absorber obtained from reaction of hydroxybenzophenone with an epoxy-containing alkoxysilane in the presence of an ammonium salt catalyst. JP-A 2000-160130 discloses a curable UV absorber obtained from reaction of tetrahydroxybenzophenone with an isocyanato-containing alkoxysilane in the presence of a tin catalyst. In these patents, links are formed in the structure of Ph—O—$CH_2$—CH(OH)— and Ph—O—C(O)—NH—, respectively. In both cases, the final reaction products are highly hydrophilic and susceptible to hydrolysis, and form UV-absorbing films on the substrate surface which are insufficient in durable adhesion under humid atmosphere. In addition, the catalyst can be left in the final reaction product, exerting detrimental effects on shelf stability.

JP-A H07-278525 and JP 3648280 disclose a curable UV absorber having only one alkoxysilane obtained by converting hydroxybenzophenone into allyl ether form and reacting it with hydrosilane, and a UV-absorbing film comprising the same. Since the hydroxybenzophenone alkyl ether alkoxysilane is an alkoxysilane having a very large substituent, it has the drawback that it is rather unsusceptible to hydrolysis, ineffective to form a film by itself, and less adhesive.

JP-A S57-21390 discloses a UV absorber having an alkoxysilyl group incorporated into a benzophenone skeleton via an amide bond. However, a composition comprising the same is less adhesive to substrates. JP-A S57-21476 discloses a UV absorber encompassing the benzophenone derivative (I-a) according to the present invention. However, the UV absorber produced by the disclosed method has the serious problem that it tends to condensate into a polymer or gel. JP-A S58-213075 discloses a UV absorber which is similar to that of JP-A S57-21476, wherein the alkoxy group bonded to silicon is changed so as to prevent the compound from gelation. Undesirably the production process is complex.

CITATION LIST

Patent Document 1: JP 4092522
Patent Document 2: JP-A 2000-160130
Patent Document 3: JP-A H07-278525
Patent Document 4: JP 3648280
Patent Document 5: JP-A S57-21390
Patent Document 6: JP-A S57-21476
Patent Document 7: JP-A S58-213075

SUMMARY OF INVENTION

An object of the invention is to provide a novel reactive UV absorber which is curable at room temperature and minimized in bleed-out, a UV-screening film-forming curable coating solution comprising the same, a UV-screening film resulting from curing of the coating solution, having improved adhesion and minimal changes with time, and a substrate having the UV-screening film formed thereon and thus displaying a UV-screening function.

The inventor has found that a mixture of a benzophenone derivative having hydroxyl and alkoxysilyl groups and a benzophenone derivative having silyloxy and alkoxysilyl groups becomes a reactive UV absorber which is unlikely to gel, stable during shelf storage, little bleeding, and curable at room temperature. This reactive UV absorber in which silicon is linked to benzophenone via a non-hydrolyzable alkyl ether bond is bondable to a substrate, and even when used alone, readily forms a UV-absorbing film having improved formability and adhesion.

It has also been found that a UV-screening film-forming coating solution comprising the reactive UV absorber, a diluent, and a curing catalyst is curable at room temperature and cures into a hard UV-screening film having improved adhesion and minimized changes with time.

Specifically, the reactive UV absorber of the invention has reactive alkoxysilyl groups on benzophenone structure having UV absorptivity wherein this linking chemical structure is resistant to hydrolysis. The absorber has the structure capable of forming a film exhibiting improved adhesion. A UV-screening film is obtainable by applying onto a substrate a UV-screening film-forming coating solution comprising the reactive UV absorber and curing the same. The film prevents the UV absorber from bleeding out and experiences minimized degradation of UV absorptivity.

Accordingly the invention provides a reactive UV absorber, a UV-screening film-forming curable coating solution, a UV-screening film, and a substrate displaying a UV-screening function, which are as defined below.

In a first embodiment, the invention provides a reactive UV absorber comprising in admixture, (I-a) a benzophenone derivative of formula (I) wherein $A^{10}$ is hydroxyl and (I-b) a benzophenone derivative of formula (I) wherein $A^{10}$ is a group of formula (b).

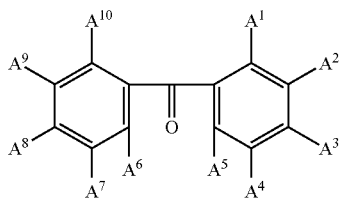

(I)

Herein $A^1$ is any one of groups represented by $A^2$ to $A^{10}$, $A^2$ to $A^9$ are hydrogen, hydroxyl, $C_1$-$C_5$ alkyl, $C_1$-$C_5$ alkoxy, or a group of formula (a):

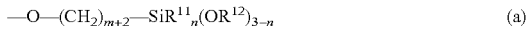

(a)

wherein $R^{11}$ and $R^{12}$ each are $C_1$-$C_5$ alkyl, m is an integer of 1 to 5, and n is an integer of 0 to 2, at least one of $A^1$ to $A^9$ being a group of formula (a), and $A^{10}$ is hydroxyl or a group of formula (b):

(b)

wherein $R^{11}$, $R^{12}$ and n are as defined above.

In a preferred embodiment, benzophenone derivatives (I-a) and (I-b) are present in a weight ratio of from 50:50 to 99:1. In formulae (a) and (b), $R^{12}$ is preferably methyl or ethyl.

A second embodiment provides a room temperature curable coating liquid or solution for forming a UV-screening film, comprising a reactive UV absorber, a diluent, and a curing catalyst, said reactive UV absorber comprising the reactive UV absorber of the first embodiment. Typically the curing catalyst comprises a titanium or aluminum compound.

A third embodiment provides a UV-screening film obtained by applying the coating solution to a substrate and curing.

A fourth embodiment provides a substrate having a UV-screening function, comprising the UV-screening film on the substrate.

ADVANTAGEOUS EFFECTS OF INVENTION

The reactive UV absorber has improved shelf stability. The UV-screening film-forming coating solution comprising the same is curable at room temperature, and forms a UV-screening film which prevents the UV absorber from bleeding out, is fully adherent to glass and plastic substrates, and is resistant to flaw by external scratch or to separation with the lapse of time. Thus substrates are provided with a long term stable UV-screening function.

DESCRIPTION OF EMBODIMENTS

A first embodiment of the invention is a reactive UV absorber comprising in admixture, (I-a) a benzophenone derivative of the general formula (I) wherein $A^{10}$ is hydroxyl and (I-b) a benzophenone derivative of formula (I) wherein $A^{10}$ is a group of formula (b).

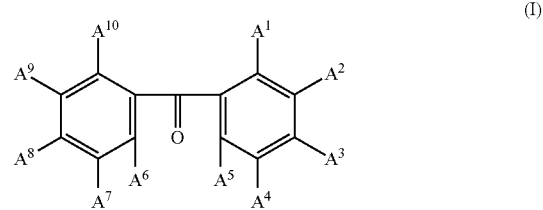

(I)

Herein $A^1$ is any one of groups represented by $A^2$ to $A^{10}$, $A^2$ to $A^9$ are hydrogen, hydroxyl, $C_1$-$C_5$ alkyl, $C_1$-$C_5$ alkoxy, or a group of formula (a):

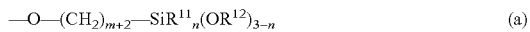

(a)

wherein $R^{11}$ and $R^{12}$ each are $C_1$-$C_5$ alkyl, m is an integer of 1 to 5, and n is an integer of 0 to 2, at least one of $A^1$ to $A^9$ being a group of formula (a), and $A^{10}$ is hydroxyl or a group of formula (b):

(b)

wherein $R^{11}$, $R^{12}$ and n are as defined above.

In formula (I), $A^1$ is any one of groups represented by $A^2$ to $A^{10}$. $A^2$ to $A^9$ are each independently selected from hydrogen, hydroxyl, $C_1$-$C_5$ alkyl such as methyl, ethyl, propyl, isopropyl, butyl, isobutyl, tert-butyl, pentyl and neopentyl, $C_1$-$C_5$ alkoxy such as methoxy, ethoxy, propoxy, isopropoxy, butoxy, isobutoxy, sec-butoxy, and tert-butoxy, and groups of formula (a). At least one of $A^1$ to $A^9$ is a group of formula (a).

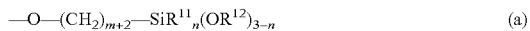

(a)

In formula (a), $R^{11}$ and $R^{12}$ are each independently selected from $C_1$-$C_5$ alkyl such as methyl, ethyl, propyl, isopropyl, butyl, isobutyl, tert-butyl, pentyl and neopentyl. Preferably $R^{11}$ is methyl, and $R^{12}$ is methyl or ethyl, more preferably methyl. The subscript m is an integer of 1 to 5, preferably 1 to 3, and n is an integer of 0 to 2, preferably 0 or 1, and more preferably 0.

$A^{10}$ is hydroxyl or a group of formula (b):

(b)

wherein $R^{11}$, $R^{12}$ and n are as defined above.

Preferably, $A^1$ is hydrogen or $A^{10}$, i.e., hydroxyl or a group of formula (b); $A^2$, $A^4$ to $A^7$, and $A^9$ are hydrogen, $A^3$ is hydrogen or a group of formula (a); and $A^8$ is a group of formula (a).

The reactive UV absorber comprises a mixture of (I-a) a benzophenone derivative of formula (I) wherein $A^{10}$ is hydroxyl and (I-b) a benzophenone derivative of formula (I) wherein $A^{10}$ is a group of formula (b). The benzophenone derivative (I-a) is a known UV absorber and suffers from the problem of shelf instability because hydrolysis and condensation readily takes place between a weakly acidic hydroxyl group and an acid so that it may become polymeric or gel. When the benzophenone derivative (I-a) is combined with the benzophenone derivative (I-b) wherein the hydroxyl group $A^{10}$ is blocked with $-OSiR^{11}_n(OR^{12})_{3-n}$, a significant improvement in shelf stability is achieved, and a coating solution comprising the mixture is able to form a stable cured film.

In the UV absorber, benzophenone derivatives (I-a) and (I-b) are preferably present in a weight ratio of from 50:50 to 99:1, more preferably from 60:40 to 98:2, and more preferably from 80:20 to 97:3. Outside the range, too high a proportion of benzophenone derivative (I-a) may lead to insufficient shelf stability whereas too low a proportion of benzophenone derivative (I-a) may lead to degraded UV absorption and increased cost.

The UV absorber may be prepared by synthesizing benzophenone derivatives (I-a) and (I-b) separately and mixing them. Preferably the absorber is prepared by the following method.

A benzophenone having at least two hydroxyl groups represented by the general formula (II):

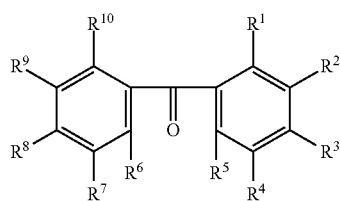

(II)

wherein $R^1$ to $R^9$ are each independently selected from hydrogen, hydroxyl, $C_1$-$C_5$ alkyl such as methyl, ethyl, propyl, isopropyl, butyl, isobutyl, tert-butyl, pentyl and neopentyl, and $C_1$-$C_5$ alkoxy such as methoxy, ethoxy, propoxy, isopropoxy, butoxy, isobutoxy, sec-butoxy, and tert-butoxy, at least one of $R^1$ to $R^9$ being hydroxyl, and $R^{10}$ is hydroxyl, is reacted with an aliphatically unsaturated compound of the general formula (III):

(III)

wherein X is a halogen atom selected from iodine, bromine and chlorine, and m is an integer of 1 to 5, preferably 1 to 3, to synthesize a benzophenone having an aliphatic unsaturated group of the formula (c):

—O—$(CH_2)_m$—CH=$CH_2$ (c)

wherein m is as defined above, which is, in turn, reacted with a hydro-containing alkoxysilane of the formula (IV):

H—$SiR^{11}_n(OR^{12})_{3-n}$ (IV)

wherein $R^{11}$ and $R^{12}$ are selected from $C_1$-$C_5$ alkyl such as methyl, ethyl, propyl, isopropyl, butyl, isobutyl, tert-butyl, pentyl and neopentyl and n is an integer of 0 to 2, preferably 0 or 1, in the presence of a platinum catalyst, thus producing the desired UV absorber.

The benzophenone having at least two hydroxyl groups represented by the general formula (II), one of the reactants used in the above process, may be readily prepared as a polyhydroxybenzophenone by reaction of a phenol having at least two hydroxyl groups with an aromatic carboxylic acid (see JP-A H05-70397, for example).

Examples of benzophenone of formula (II) include 2,4-dihydroxybenzophenone, 2,3,4-trihydroxybenzophenone, 2,4,4'-trihydroxybenzophenone, 2,2',4-trihydroxybenzophenone, 2,2',3,4-tetrahydroxybenzophenone, 2,3,4,4'-tetrahydroxybenzophenone, 2,2',4,4'-tetrahydroxybenzophenone, 2,2',3,4,4'-pentahydroxybenzophenone, 2,3-dihydroxy-4-methoxybenzophenone, 2,2'-dihydroxy-4-methoxybenzophenone, 2,4-dihydroxy-4'-methoxybenzophenone, 2,2'-dihydroxy-3,3-dimethoxybenzophenone, 2,3-dihydroxy-4,4'-dimethoxybenzophenone, 2,2'-dihydroxy-4,4'-dimethoxybenzophenone, 4-methoxy-2,2',4'-trihydroxybenzophenone, 4-butoxy-2,2',4'-trihydroxybenzophenone, and 3,4-dimethoxy-2,2',4'-trihydroxybenzophenone.

The benzophenone having an aliphatic unsaturated group of formula (c) may be readily prepared as an ether bond-bearing benzophenone by reacting a hydroxyl group on the benzophenone having at least two hydroxyl groups represented by formula (II) with a halogen atom on the aliphatically unsaturated compound represented by formula (III).

Specifically the benzophenone having an aliphatic unsaturated group of formula (c) may be readily synthesized by reacting the compound of formula (II) with the compound of formula (III) such as allyl chloride, allyl bromide or allyl iodide, in the presence of a base such as an alkali metal hydroxide, alkaline earth metal hydroxide, alkali metal alkoxide, alkaline earth metal alkoxide, alkali metal carbonate, alkaline earth metal carbonate, or amine, and optionally in an inert solvent such as a ketone, ester or ether. This reaction may be effected at room temperature to about 200° C., preferably 50° C. to 150° C. Typically the reaction is completed within about 30 minutes to about 10 hours when conducted at an elevated temperature of about 120° C.

For the reaction, the compound of formula (II) and the compound of formula (III) are in such amounts that the hydroxyl groups on the compound of formula (II) are in molar excess relative to the halogen atoms on the compound of formula (III). Preferably, the compound of formula (III) having a halogen atom (typically one) is present in an amount to give (n–1) mole to ((n–1)+0.5) mole, and more preferably (n–1) mole to ((n–1)×1.1) mole of halogen per mole of the compound of formula (II) having n hydroxyl groups. In one example where the compound of formula (II) has two hydroxyl groups, the compound of formula (III) is preferably used in an amount of 1 to 1.5 moles, more preferably 1 to 1.1 moles per mole of the compound of formula (II). In another example where the compound of formula (II) has three hydroxyl groups, the compound of formula (III) is preferably used in an amount of 2 to 2.5 moles, more preferably 2 to 2.2 moles per mole of the compound of formula (II).

The resulting reaction product, benzophenone having an aliphatic unsaturated group of formula (c) corresponds to formula (I) wherein the group of formula (a) is replaced by the group of formula (c).

Next, the benzophenone having an aliphatic unsaturated group of formula (c) is reacted with a hydro-alkoxysilane of formula (IV) (specifically aliphatic unsaturated group is reacted with hydrosilyl group) in the presence of chloroplatinic acid or a catalyst for siloxane systems, optionally in an inert solvent such as toluene or tetrahydrofuran or in a solventless system. In this way, the UV absorber is readily synthesized.

The hydro-alkoxysilane of formula (IV) is a hydrosilane compound having 1 to 3 methoxy, ethoxy, propoxy, butoxy or similar groups. Examples include trimethoxysilane, triethoxysilane, tripropoxysilane, tributoxysilane, dimethoxymethylsilane, diethoxymethylsilane, dipropoxymethylsilane, and dibutoxymethylsilane. Inter alia, trimethoxysilane and triethoxysilane are preferred.

The reaction may be effected at room temperature to about 200° C., and preferably about 30° C. to about 100° C. When trimethoxysilane is used, the reaction is completed within about 30 minutes to about 2 hours at an elevated temperature from room temperature to about 60° C.

For the reaction, the benzophenone having an aliphatic unsaturated group of formula (c) and the alkoxysilane of formula (IV) are combined such that the alkoxysilane of formula (IV) is in excess per mole of the aliphatic unsaturated group on the benzophenone having an aliphatic unsaturated group of formula (c), preferably 1.01 to 2 moles, more preferably 1.1 to 1.5 moles per mole of the aliphatic unsaturated group. The reaction within this range ensures that the alkoxysilane of formula (IV) reacts with some or all of hydroxyl groups present in the benzophenone having an aliphatic unsaturated group of formula (c) to create groups of formula (b), thereby yielding a mixture consisting of benzophenone derivatives (I-a) and (I-b) in a desired ratio.

A second embodiment of the invention is a curable coating solution or liquid for forming a UV-screening film, comprising a reactive UV absorber, a diluent solvent, and a curing catalyst, wherein at least part or all of the reactive UV absorber compounded herein is the reactive UV absorber of the first embodiment. The coating solution is curable at room temperature and may be used as a coating composition known as silicone hard-coat or topcoat.

The UV-screening film-forming curable coating solution comprises at least the reactive UV absorber of the first embodiment as its reactive UV absorber component. Cure takes place as hydrolysis of alkoxysilyl groups on the reactive UV absorber, followed by polycondensation of silanol into a polymer. The reactive UV absorber by itself forms a cured film, without a need for another binder component. The coating resulting from polymerization of the UV absorber itself is tough and robust enough to prevent the UV absorber from bleeding out. Depending on a particular application, a binder component as used in coating compositions in that application may be added.

As the reactive UV absorber in the UV-screening film-forming curable coating solution, the reactive UV absorber of the first embodiment may be used alone or in combination with another UV absorber. The other UV absorber used in combination is not particularly limited, and inorganic UV absorbers such as ZnO, $CeO_2$ and $TiO_2$ may be used. When combined with the other UV absorber, the reactive UV absorber of the first embodiment is preferably used in an amount of 30 to 100% by weight, and more preferably 50 to 100% by weight of the entire reactive UV absorber. If the amount of the reactive UV absorber of the first embodiment is too small, a cured film having a superior UV absorbing function may not be formed.

For common applications, the reactive UV absorber is desirably present in an amount of 5 to 60% by weight of the coating solution. If the concentration is less than 5% by weight, the coating solution may cure into a film having poor UV screening function. If the concentration is more than 60% by weight, the coating solution may experience a viscosity buildup to interfere with coating operation even when no other solids are added.

When the UV absorber other than the reactive UV absorber of the first embodiment is used in combination, the coating solution may have a lower reactive UV absorber concentration than the above-range. Even at a concentration of 1 to 12% by weight, specifically 1 to 6% by weight, a curable coating solution which is practically acceptable is available.

A curing catalyst is added to the reactive UV absorber to formulate a UV-screen film-forming curable coating solution in order that the coating solution be humidity curable and have a practically acceptable cure rate at room temperature. Suitable curing catalysts include acids such as hydrochloric acid, sulfuric acid and para-toluenesulfonic acid, bases such as triethylamine, tributylamine, and tetrabutylammonium hydroxide, and tin, aluminum and titanium compounds such as dibutyltin octate, aluminum acetylacetonate, and titanium tetrabutoxide. Inter alia, titanium and aluminum compounds are preferred, with titanium tetrabutoxide and aluminum acetylacetonate being most preferred.

The curing catalyst may be used in a catalytic amount, preferably in an amount of 0.01 to 10 parts, more preferably 0.1 to 5 parts by weight per 100 parts by weight of the UV absorber of the first embodiment. Too small an amount of the catalyst may lead to under-cure whereas a coating solution containing too large an amount of the catalyst may be likely to gel.

The diluent solvent used in the UV-screen film-forming curable coating solution is not particularly limited, and may be selected in accordance with coating conditions, coating environment, and the type of solid in the coating solution. Suitable diluents include alcohols such as methanol, ethanol and isobutyl alcohol; ether alcohols such as ethylene glycol monomethyl ether and ethylene glycol monoethyl ether; esters such as methyl acetate and ethyl acetate; and ketones such as methyl ethyl ketone and cyclohexanone. Depending on a particular application, the solvents may be used alone or in combination. A compound having ketone and alcohol in a molecule like diacetone alcohol is also useful. For substrates made of polycarbonate resins, diacetone alcohol is preferred as the solvent which does not attack the substrates and in which the reactive UV absorber is highly soluble. When no binder resin is used, the amount of the diluent solvent used is preferably 100 to 2,000 parts, more preferably 200 to 1,000 parts by weight per 100 parts by weight of the UV absorber of the first embodiment. When a binder resin is added, the diluent solvent is preferably used in such amounts that the coating solution may have a concentration of 5 to 50% by weight of solids.

Solid components other than the reactive UV absorber may be added to the UV-screen film-forming curable coating solution, for example, inorganic ultra-fine particles such as colloidal silica, $Al_2O_3$, $TiO_2$ and $ZrO_2$, and various silane coupling agents alone or in admixture. The addition of such a solid component improves the applicability of the coating solution, the hardness of a coating film, adhesion to substrates, and the like. The amount of solid component other than the reactive UV absorber is preferably 0 to 50% by weight, and more preferably 1 to 30% by weight of the UV-screen film-forming curable coating solution.

The UV-screen film-forming curable coating solution may be prepared by mixing the components in a standard way.

In a third embodiment of the invention, the UV-screen film-forming curable coating solution thus obtained is applied onto a substrate such as glass, plastics or film and cured at room temperature to form a UV-screening film having a UV-screening function with long-term stability.

In a fourth embodiment of the invention, the UV-screen film-forming curable coating solution is applied onto a surface of a solid substrate as a silicone hard-coat or UV-curable coating, thereby providing a coated solid substrate having improved abrasion resistance and UV resistance. The coated solid substrate is often referred to as weather resistant substrate.

Examples of the solid substrate which can be used herein include polycarbonate, acrylic polymers such as poly(methyl methacrylate), polyesters such as polyethylene terephthalate) and poly(butylene terephthalate), polyamides, polyimides, acrylonitrile-styrene copolymers, styrene-acrylonitrile-butadiene copolymers, polyvinyl chloride, polystyrene, polystyrene/polyphenylene ether blends, polybutyrate and polyethylene. Such thermoplastic substrates may or may not contain pigments. Suitable solid substrates further include metal substrates, glass, ceramics and textiles. Those substrates whose surface is coated with various coating compositions are also envisioned.

The method of applying the UV-screen film-forming curable coating solution is not particularly limited. Suitable methods include spin coating, spray coating, dip coating, screen printing, coating with fabrics or brushes, and similar methods capable of applying a coating solution as a thin uniform coating. The UV-screening film formed on a substrate provides the substrate with a UV-screening function having long-term stability, and prevents the substrate from degradation by UV exposure. Then the substrate having the UV-screening film formed thereon maintains a UV-screening function over a long time.

The thickness of a coating of the UV-screen film-forming curable coating solution is not particularly limited and may be suitably selected in accordance with a particular purpose of use and a particular application. Typically the coating or film has a thickness of 0.5 to 50 μm, and preferably 1 to 15 μm.

EXAMPLE

Synthesis Examples, Preparation Examples, Examples and Comparative Examples are given below for further illustrating the invention although the invention is not limited to the Examples.

First, the synthesis of reactive UV absorbers is described. It is noted that 4-allyloxy-2-hydroxybenzophenone is commercially available from Aldrich.

Synthesis Example 1

Synthesis of Allylated UV Absorber

A flask equipped with a thermometer and heater/reflux setup was charged with 100 g (0.406 mol) of 2,2',4,4'-tetrahydroxybenzophenone and 500 g of methyl isobutyl ketone (MIBK), which were stirred into a solution. To the solution were added 100 g (0.82 mol) of allyl bromide and 138 g (1 mol) of anhydrous potassium carbonate. With vigorous stirring, the contents were heated at 110° C. for 5 hours using an oil bath.

The salt formed, potassium bromide was filtered off. By vacuum stripping, the solvent MIBK was removed from the reaction solution. There was obtained about 100 g of 2,2'-dihydroxy-4,4'-diallyloxybenzophenone as a red viscous oil. Methanol was added to the oil for crystallization. By filtration, 8.6 g (0.272 mol) of 2,2'-dihydroxy-4,4'-diallyloxybenzophenone was recovered as yellow solids (yield 67%, melting point 95° C.).

Synthesis Example 2

Synthesis of Silylated UV Absorber 1

In 70 ml of toluene was suspended 32.6 g (0.1 mol) of 2,2'-dihydroxy-4,4'-diallyloxybenzophenone. Two droplets of platinum catalyst PL50-T (Shin-Etsu Chemical Co., Ltd.) were added to the suspension, which was heated to a temperature of 65° C. before 29.3 g (0.24 mol) of trimethoxysilane was added.

The temperature was maintained at about 65-85° C. for about 1-2 hours, after which the reaction mixture was cooled. Silica gel Wakogel® C-100, 5 g, was added, on which the platinum catalyst was adsorbed. Filtration and subsequent vacuum stripping of the solvent yielded 51.9 g (0.091 mol) of a red oily matter. The NMR spectrum of the main product was coincident with the structure of 2,2'-substituted-4,4'-bis(trimethoxysilylpropoxy)benzophenone (yield 91%). It was a mixture consisting of 2,2'-dihydroxy-4,4'-bis(trimethoxy-silylpropoxy)benzophenone:2-hydroxy-2'-trimethoxysilyloxy-4,4'-bis(trimethoxysilylpropoxy)benzophenone:2,2'-bis(tri-methoxysilyloxy)-4,4'-bis(trimethoxysilylpropoxy) benzophenone in a weight ratio of 71:11:17. This silane is abbreviated as UVsilane #1.

Synthesis Example 3

Synthesis of Silylated UV Absorber 2

In 70 ml of toluene was suspended 25.4 g (0.1 mol) of 4-allyloxy-2-hydroxybenzophenone. Two droplets of platinum catalyst PL50-T (Shin-Etsu Chemical Co., Ltd.) were added to the suspension, which was heated to a temperature of 65° C. before 31.7 g (0.26 mol) of trimethoxysilane was added.

The temperature was maintained at about 65-85° C. for about 1-2 hours, after which the reaction mixture was cooled. Silica gel Wakogel® C-100, 5 g, was added, on which the platinum catalyst was adsorbed. Filtration and subsequent vacuum stripping of the solvent yielded 34.8 g (0.092 mol) of a yellow oily matter. The NMR spectrum of the main product was coincident with the structure of 2-substituted-4-trimethoxysilylpropoxybenzophenone (yield 92%). It was a mixture consisting of 2-hydroxy-4-trimethoxysilylpropoxy-benzophenone:2-trimethoxysilyloxy-4-trimethoxysilylpropoxy-benzophenone in a weight ratio of 90:10. This silane is abbreviated as UVsilane #2.

Comparative Synthesis Example 1

Synthesis of Silylated UV Absorber 3

In 70 ml of toluene was suspended 25.4 g (0.1 mol) of 4-allyloxy-2-hydroxybenzophenone. Two droplets of platinum catalyst PL50-T (Shin-Etsu Chemical Co., Ltd.) were added to the suspension, which was heated to a temperature of 40° C. before 24.4 g (0.2 mol) of trimethoxysilane was added.

The temperature was maintained at about 35-45° C. for about 1-2 hours, after which the reaction mixture was cooled. Silica gel Wakogel® C-100, 5 g, was added, on which the platinum catalyst was adsorbed. Filtration and subsequent vacuum stripping of the solvent yielded 23.4 g (0.062 mol) of an orange oily matter. The NMR spectrum of the main product was coincident with the structure of 2-hydroxy-4-trimethoxy-silylpropoxybenzophenone containing some unreacted reactant (yield 62%). This silane is abbreviated as UVsilane #3.

These silylated UV absorbers were measured for UV absorption spectrum peak wavelength (in 0.01 wt % THF solution), with the data shown in Table 1. It is seen that a compound having more phenolic hydroxyl groups in a molecule exhibits greater absorption in the near-ultraviolet region.

TABLE 1

| | Synthesis Example 2 | Synthesis Example 3 | Comparative Synthesis Example 1 |
|---|---|---|---|
| UV absorber | UVsilane #1 | UVsilane #2 | UVsilane #3 |
| Appearance | red oil | yellow oil | orange oil |
| Peak absorption wavelength | 321, 283, 213 nm | 278, 238, 210 nm | 326, 284, 242 nm |

TABLE 1-continued

|  | Synthesis Example 2 | Synthesis Example 3 | Comparative Synthesis Example 1 |
|---|---|---|---|
| Absorption in UVA (320-400 nm) | high | low | noticeable |

Described below are coating solutions comprising reactive UV absorbers.

Preparation Example 1

Reactive UV absorber UVsilane #1 (10 g) was added to 90 g of methyl ethyl ketone (MEK) and stirred until the absorber was homogeneously dissolved. Aluminum acetylacetonate (0.2 g) as a curing catalyst was added to the solution, which was stirred to give a UV screen film-forming curable coating solution, designated 1-M-Al.

Preparation Example 2

Reactive UV absorber UVsilane #1 (10 g) was added to 90 g of MEK and stirred until the absorber was homogeneously dissolved. Tetrabutoxytitanate (0.2 g) as a curing catalyst was added to the solution, which was stirred to give a UV screen film-forming curable coating solution, designated 1-M-Ti.

Comparative Preparation Example 1

Reactive UV absorber UVsilane #3 (10 g) was added to 90 g of MEK and stirred until the absorber was homogeneously dissolved. Aluminum acetylacetonate (0.2 g) as a curing catalyst was added to the solution, which was stirred to give a UV screen film-forming curable coating solution, designated 3-M-Al.

Comparative Preparation Example 2

Reactive UV absorber UVsilane #3 (10 g) was added to 90 g of MEK and stirred until the absorber was homogeneously dissolved. Tetrabutoxytitanate (0.2 g) as a curing catalyst was added to the solution, which was stirred to give a UV screen film-forming curable coating solution, designated 3-M-Ti.

Preparation Example 3

Reactive UV absorber UVsilane #2 (10 g) was added to 90 g of MEK and stirred until the absorber was homogeneously dissolved. Aluminum acetylacetonate (0.2 g) as a curing catalyst was added to the solution, which was stirred to give a UV screen film-forming curable coating solution, designated 2-M-Al.

Preparation Example 4

Reactive UV absorber UVsilane #2 (10 g) was added to 90 g of MEK and stirred until the absorber was homogeneously dissolved. Tetrabutoxytitanate (0.2 g) as a curing catalyst was added to the solution, which was stirred to give a UV screen film-forming curable coating solution, designated 2-M-Ti.

Table 2 shows the composition and physical properties of the coating solutions in the foregoing Preparation Examples. The physical properties (appearance, refractive index, viscosity and nonvolatile) of coating solution were evaluated by the following methods.

Appearance

A transparent glass vial was filled with the coating solution, whose color and state were visually observed.

Refractive Index

Using a refractometer RX-7000 (Atago Co., Ltd.), a refractive index was measured at 25° C.

Viscosity

Using a capillary dynamic viscometer (Sibata Scientific Technology Ltd.), a viscosity was measured at 25° C.

Nonvolatile

A sample was placed in an aluminum dish, which was held in an oven at 105° C. for 3 hours. A heat loss was determined, from which a nonvolatile content was calculated.

Examples 1 to 4 & Comparative Examples 1, 2

Each of the UV screen film-forming curable coating solutions in Preparation Examples was cast over a soda-lime glass substrate of 3 mm thick to give a coating over the entire surface thereof. The coating was allowed to cure at room temperature (25° C.) for one day, forming a UV-screen film.

The UV-screen films thus obtained were measured for appearance, thickness, surface state, UV cutoff wavelength, adhesion, and hardness by the following methods. The film properties are shown in Table 2.

Appearance

A film on the glass substrate was visually observed.

Thickness

The thickness of a film was measured by a micrometer (Mitutoyo Corp.).

Surface State

A film on the glass substrate was examined for tack by a finger touch. A sample is rated "tack-free" when it is not sticky and "tacky" when it is sticky and bears the finger mark.

UV Cutoff Wavelength

The transmittance of a film was measured by a spectrophotometer. U-3310 (Hitachi Ltd.) and the cutoff wavelength of blocking UV transmission was calculated. Note that the UV cutoff wavelength of the glass substrate was 280 nm.

Adhesion

A cross-hatch adhesion test was performed. A film was scribed along 6×6 lines in a region of 1 cm by 1 cm to define a pattern of 25 square sections. Adhesive tape Cellophane® (Nitto Denko Co., Ltd.) was attached thereto and pulled apart. A sample is rated good (or 100%) when no sections are peeled. When some sections are peeled off, a sample is rated in terms of the area percent of remaining sections.

Hardness

After coating and curing, a film was held one day and examined by scratching its surface with nail. It was rated according to the following criterion.

○: film was not flawed with nail

Δ: film was slightly flawed with nail

X: film was flawed with nail

NG: unmeasurable

Whether Al or Ti catalyst was used, the coating solutions containing UVsilane #3 failed to form satisfactory films. The coating solutions containing UVsilane #1 or #2 formed satisfactory films, particularly when Al catalyst was used.

TABLE 2

| | | | Example | | Comparative Example | | Example | |
|---|---|---|---|---|---|---|---|---|
| | | | 1 | 2 | 1 | 2 | 3 | 4 |
| Composition of coating solution | UVsilane | Amount 10 | #1 | #1 | #3 | #3 | #2 | #2 |
| | Solvent | (g) 90 | MEK | MEK | MEK | MEK | MEK | MEK |
| | Catalyst | 0.2 | Al | Ti | Al | Ti | Al | Ti |
| | Designation | | 1-M-Al | 1-M-Ti | 3-M-Al | 3-M-Ti | 2-M-Al | 2-M-Ti |
| Physical properties of coating solution | Appearance | | clear solution | yellow solution | clear solution | yellow solution | clear solution | yellow solution |
| | Refractive index | | 1.3912 | 1.3914 | 1.3883 | 1.3882 | 1.3877 | 1.388 |
| | Viscosity (mm$^2$/s) | | 0.56 | 0.57 | 0.6 | 0.57 | 0.59 | 0.62 |
| | Nonvolatile (%) @105° C./3 hr | | 8.05 | 8.18 | 8.26 | 8.37 | 8.38 | 8.76 |
| Physical properties of film | Appearance or film formability | | clear film | yellow clear film | clear film | not cured | clear film | yellow clear film |
| | Thickness (μm) | | 10 | 10 | 11 | — | 11 | 6 |
| | Surface state | | tack-free | tack-free | tack-free | — | tack-free | tacky |
| | UV cutoff wavelength nm (Abs > 0.1) | | 424 | 463 | 418 | — | 400 | 438 |
| | Adhesion | | good | good | good | NG | good | good |
| | Hardness | | ○ | Δ | X | NG | ○ | Δ |

UVsilane
UVsilane #1: silylated UV absorber in Synthesis Example 2
UVsilane #2: silylated UV absorber in Synthesis Example 3
UVsilane #3: silylated UV absorber in Comparative Synthesis Example 1
Solvent
MEK: methyl ethyl ketone
Catalyst
Al: Al(acac)$_3$
Ti: tetrabutoxytitanate Preparation Example 5

Reactive UV absorber UVsilane #1 (10 g) was added to 90 g of diacetone alcohol (DAA) and stirred until the absorber was homogeneously dissolved. Tetrabutoxytitanate (0.2 g) as a curing catalyst was added to the solution, which was stirred to give a UV screen film-forming curable coating solution, designated 1-D-Ti.

Preparation Example 6

Reactive UV absorber UVsilane #2 (10 g) was added to 90 g of DAA and stirred until the absorber was homogeneously dissolved. Tetrabutoxytitanate (0.2 g) as a curing catalyst was added to the solution, which was stirred to give a UV screen film-forming curable coating solution, designated 2-D-Ti.

Comparative Preparation Example 3

Reactive UV absorber UVsilane #3 (10 g) was added to 90 g of DAA and stirred until the absorber was homogeneously dissolved. Tetrabutoxytitanate (0.2 g) as a curing catalyst was added to the solution, which was stirred to give a UV screen film-forming curable coating solution, designated 3-D-Ti.

Table 3 shows the composition and physical properties of the coating solutions in the foregoing Preparation Examples. The physical properties (appearance, viscosity and nonvolatile) of coating solution were evaluated by the above methods.

Examples 5, 6 & Comparative Example 3

Each of the UV screen film-forming curable coating solutions in Preparation Examples was cast over a polycarbonate substrate (Iupilon NF2000 by Mitsubishi Engineering-Plastics Corp., 0.5 mm thick, clear sheet) to give a coating over the entire surface thereof. The coating was cured at 105° C. for one hour, forming a UV-screen film.

The UV-screen films thus obtained were measured for appearance, thickness, hardness, adhesion, and boiling adhesion by the following methods. The film properties are shown in Table 3.

Appearance

A film on the polycarbonate substrate was visually observed.

Thickness

The thickness of a film was measured by Thin Film Analyzer F20 (Filmetrics).

Hardness

After coating and curing, a film was allowed to cool to room temperature and examined by scratching its surface with nail. It was rated according to the following criterion.

○: film was not flawed with nail

Δ: film was slightly flawed with nail

X: film was flawed with nail

NG: unmeasurable

Adhesion

A cross-hatch adhesion test was performed by scribing a film with a cutter to define a pattern of square sections, attaching and pulling apart adhesive tape.

Boiling Adhesion

A film was immersed in boiling water at 100° C. for 2 hours before it was examined for durability by the same cross-hatch adhesion test.

The coating solution containing UVsilane #3 formed an unsatisfactory film which was poor in hardness and initial adhesion. The coating solution containing UVsilane #2 formed a film which was satisfactory in hardness and initial adhesion. The coating solution containing UVsilane #1 formed a film which was satisfactory even in boiling adhesion, i.e., exhibited fully durable adhesion.

TABLE 3

| | | | Example 5 | Example 6 | Comparative Example 3 |
|---|---|---|---|---|---|
| Composition of coating solution | UVsilane | Amount (g) | #1 10 | #2 10 | #3 10 |
| | Solvent | | DAA 90 | DAA 90 | DAA 90 |
| | Catalyst | | Ti 0.2 | Ti 0.2 | Ti 0.2 |
| | Designation | | 1-D-Ti | 2-D-Ti | 3-D-Ti |
| Physical properties of coating solution | Appearance | | yellow solution | yellow solution | yellow solution |
| | Nonvolatile (%) @105° C./3 hr | | 8.88 | 9.71 | 8.05 |
| | Viscosity (mm²/s) | | 4.02 | 3.99 | 3.98 |
| Physical properties of film | Appearance | | faintly yellow clear film | faintly yellow clear film | faintly yellow clear film |
| | Thickness (μm) | | 1.44 | 2.36 | 1.01 |
| | Hardness | | ○ | ○ | X |
| | Adhesion (cross-hatch test) | | 100% | 100% | 8% |
| | Adhesion after boiling 100° C./1 hr | | 100% | 50% | 0% |

UVsilane
UVsilane #1: silylated UV absorber in Synthesis Example 2
UVsilane #2: silylated UV absorber in Synthesis Example 3
UVsilane #3: silylated UV absorber in Comparative Synthesis Example 1
Solvent
DAA: diacetone alcohol
Catalyst
Ti: tetrabutoxytitanate Japanese Patent Application No. 2008-283039 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A reactive UV absorber comprising; in admixture, (I-a) a benzophenone derivative of formula (I) wherein $A^{10}$ is hydroxyl and (I-b) a benzophenone derivative of formula (I) wherein $A^{10}$ is a group of formula (b),

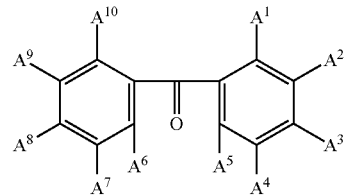

(I)

wherein $A^1$ is any one of groups represented by $A^2$ to $A^{10}$, $A^2$ to $A^9$ are hydrogen, hydroxyl, $C_1$-$C_5$ alkyl, $C_1$-$C_5$ alkoxy, or a group of formula (a):

$$-O-(CH_2)_{m+2}-SiR^{11}_n(OR^{12})_{3-n} \tag{a}$$

wherein $R^{11}$ and $R^{12}$ each are $C_1$-$C_5$ alkyl, m is an integer of 1 to 5, and n is an integer of 0 to 2, provided that at least one of $A^1$ to $A^9$ is a group of formula (a), and $A^{10}$ is hydroxyl in formula (I-a) or a group of formula (b) in formula (I-b):

$$-OSiR^{11}_n(OR^{12})_{3-n} \tag{b}$$

wherein $R^{11}$, $R^{12}$ and n are as defined above.

2. The UV absorber of claim 1 wherein benzophenone derivatives (I-a) and (I-b) are present in a weight ratio of from 50:50 to 99:1.

3. The UV absorber of claim 1 wherein in formulae (a) and (b), $R^{12}$ is methyl or ethyl.

4. A room temperature curable coating solution for forming a UV-screening film, comprising a reactive UV absorber, a diluent, and a curing catalyst, said reactive UV absorber comprising the reactive UV absorber of claim 1.

5. The coating solution of claim 4 wherein said curing catalyst comprises a titanium or aluminum compound.

6. A UV-screening film obtained by applying the coating solution of claim 4 to a substrate and curing.

7. A substrate having a UV-screening function, comprising the UV-screening film of claim 6 formed on the substrate.

* * * * *